(12) United States Patent
Cao et al.

(10) Patent No.: US 7,708,976 B2
(45) Date of Patent: May 4, 2010

(54) ALUMINOPHOSPHATE MOLECULAR SIEVE, ITS SYNTHESIS AND USE

(75) Inventors: Guang Cao, Branchburg, NJ (US); Matu J. Shah, Hackettstown, NJ (US)

(73) Assignee: ExxonMobil Chemical Patents Inc., Houston, TX (US)

(*) Notice: Subject to any disclaimer, the term of this patent is extended or adjusted under 35 U.S.C. 154(b) by 180 days.

(21) Appl. No.: 11/663,716

(22) PCT Filed: Sep. 12, 2005

(86) PCT No.: PCT/EP2005/009880

§ 371 (c)(1),
(2), (4) Date: Mar. 23, 2007

(87) PCT Pub. No.: WO2006/037437

PCT Pub. Date: Apr. 13, 2006

(65) Prior Publication Data

US 2007/0286799 A1    Dec. 13, 2007

Related U.S. Application Data

(60) Provisional application No. 60/615,228, filed on Oct. 1, 2004.

(51) Int. Cl.
*C01B 39/00* (2006.01)
*C01B 33/36* (2006.01)

(52) U.S. Cl. ........................................... 423/718

(58) Field of Classification Search .............. None
See application file for complete search history.

(56) References Cited

U.S. PATENT DOCUMENTS

| | | | | |
|---|---|---|---|---|
| 4,499,327 | A | * | 2/1985 | Kaiser ................. 585/640 |
| 5,932,512 | A | * | 8/1999 | Sun ..................... 502/214 |
| 6,680,278 | B2 | | 1/2004 | Cao et al. |
| 2003/0231999 | A1 | | 12/2003 | Cao et al. |
| 2003/0232718 | A1 | | 12/2003 | Cao et al. |
| 2006/0074267 | A1 | | 4/2006 | Cao et al. |

FOREIGN PATENT DOCUMENTS

| | | |
|---|---|---|
| EP | 0 337 479 | 10/1989 |
| EP | 0 324 082 | 8/1992 |

OTHER PUBLICATIONS

NK-101, Oct. 2001, Chemical Journal of Chinese Universities, vol. 22, No. 10, pp. 192-195.*

* cited by examiner

*Primary Examiner*—Melvin C Mayes
*Assistant Examiner*—Stefanie Cohen
(74) *Attorney, Agent, or Firm*—D. M. Tyus (57) ABSTRACT

A novel small pore (metallo)aluminophosphate molecular sieve is disclosed. The as-synthesized material has an X-ray diffraction pattern including the lines listed in Table 1 and is produced in the presence of fluoride ions and 4-dimethylaminopyridine as structure directing agent. The silicoaluminophosphate material has methanol conversion activity and n-hexane cracking activity.

28 Claims, 3 Drawing Sheets

Figure 1. XRD's of Example 1 Products

Figure 2. XRD's of Example 2 Products

Figure 3. XRD's of Example 3 Products

Figure 4. XRD's of Example 4 Products

Figure 5. XRD's of Calcined Samples

Figure 6. XRD's of Calcined Sample B

US 7,708,976 B2

ALUMINOPHOSPHATE MOLECULAR SIEVE, ITS SYNTHESIS AND USE

CROSS REFERENCE TO RELATED APPLICATIONS

This application is a National Stage Application of International Application No. PCT/EP2005/009880, filed Sep. 12, 2005, which claims the benefit of Provisional Application No. 60/615,228, filed Oct. 1, 2004, the disclosures of which are incorporated by reference in their entireties.

FIELD

This invention relates to a novel small pore aluminophosphate molecular sieve, or a substituted derivative thereof, to a method of synthesis of the molecular sieve and to its use in organic conversion reactions.

BACKGROUND

Crystalline molecular sieves have a 3-dimensional, four-connected framework structure of corner-sharing [TO$_4$] tetrahedra, where T is any tetrahedrally coordinated cation. Among the known forms of molecular sieve are aluminosilicates, which contain a three-dimensional microporous crystal framework structure of [SiO$_4$] and [AlO$_4$] corner sharing tetrahedral units, aluminophosphates (ALPOs), in which the framework structure is composed of [AlO$_4$] and [PO$_4$] corner sharing tetrahedral units and silicoaluminophosphates (SAPOs), in which the framework structure is composed of [SiO$_4$], [AlO$_4$] and [PO$_4$] corner sharing tetrahedral units.

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types*, 5th edition, Elsevier, London, England (2001), which is herein fully incorporated by reference.

Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1-67, Elsevier Science, B.V., Amsterdam, Netherlands (2001).

In general, molecular sieves can be divided into small, medium and large pore materials. Thus small pore molecular sieves typically have pores defined by a ring of no more than 8 T atoms and have an average pore size less than about 0.5 nm (5 Å). Medium pore molecular sieves typically have pores defined by a ring of 10 T atoms and have an average pore size about 0.5 to 0.6 nm (5 to 6 Å), whereas large pore materials have pores defined by rings of 12 or more T atoms and a pore size greater than 0.6 nm (6 Å).

Crystalline molecular sieves, as exemplified by zeolites and (metallo)aluminophosphates, are commercially important materials for petroleum processing and petrochemical applications. Because each unique structure type offers new potential for applications in catalysis and separations, there has been sustained research effort, both in industry and academia, for their discovery.

Many molecular sieves are synthesized in the presence of an organic directing agent, such as an organic nitrogen compound. For example, it is known from, for example, U.S. Pat. No. 6,680,278 that a crystalline silicoaluminophosphate molecular sieve of the CHA framework type (a small pore material), can be synthesized in the presence of an organic directing agent mixture comprising tetraethylammonium cations and one or more dimethylamino moieties selected from one or more of N,N-dimethylethanolamine, N,N-dimethylpropanolamine, N,N-dimethylbutanolamine, N,N-dimethylheptanolamine, N,N-dimethylhexanolamine, N,N-dimethylethylenediamine, N,N-dimethylbutylenediamine, N,N-dimethylheptylenediamine, N,N-dimethylhexylenediamine 1-dimethylamino-2-propanol, N,N-dimethylethylamine, N,N-dimethylpropylamine, N,N-dimethylpentylamine, N,N-dimethylhexylamine and N,N-dimethylheptylamine. Other organic directing agents that have been used in the synthesis of CHA framework type materials include isopropylamine or di-n-propylamine triethylamine, cyclohexylamine, 1-methylamidazole, morpholine, pyridine, piperidine, diethylethanolamine, and N,N,N',N'-tetraethylethylene diamine.

It is also known to use fluoride-containing compounds, such as hydrogen fluoride, as mineralizing agents in zeolite synthesis. For example, EP-A-337,479 discloses the use of hydrogen fluoride in water at low pH to mineralize silica in glass for the synthesis of ZSM-5. In addition, U.S. Patent Application Publication No. 2003/0231999 published Dec. 18, 2003 and incorporated herein by reference, discloses that aluminophosphate or silicoaluminophosphate molecular sieves having the CHA framework type can be synthesized in the presence of fluoride ions using the dimethylamino compounds disclosed in U.S. Pat. No. 6,680,278 as directing agents.

Currently, an entirely rational approach that leads to the synthesis of unique framework materials is not available, due to the fact that all crystalline microporous materials are metastable phases and they are kinetic products. Their discovery is therefore often serendipitous.

Our research has led to two findings: that 4-DMAPy can direct the synthesis of low-silica SAPO-CHA in the presence of colloidal SAPO-34 seeds; and, from parallel experiments, that with 4-DMAPy as an organic directing agent, without SAPO-34 seeds but in the presence of significant levels of fluoride ion F (F/Al$_2$O$_3$ of at least 0.75), there is unexpectedly formed a crystalline aluminophosphate designated EMM-9 with a new, but as yet undetermined, framework structure and having pores that in cross section have at least one distance or "diameter" that is typically categorised as small. At lower levels of fluoride ion (F/Al$_2$O$_3$<0.75), the synthesis gave a new large pore aluminophosphate, which is the subject of co-pending U.S. Patent Application Ser. No. 60/615,111 filed 1 Oct. 2004.

According to an article in the Chemical Journal of Chinese Universities, Vol. 22, No. 10, pages 192-195, dated October 2001, DMAPy has been used as a template in the synthesis of NK-101, an aluminophosphate. However, comparison of the X-ray diffraction patterns of NK-101 with that of the small pore material of the invention shows that the present material is different from NK-101.

SUMMARY

In one aspect, the invention resides in a crystalline material having, in its as-synthesized form, an X-ray diffraction pattern including the lines listed in Table 1 below. In its as-calcined form, the material of the invention has an X-ray diffraction pattern including the lines listed in Table 2 below.

The phrase "including the lines" as used herein means that peaks are expected to be present at or close to the lines indicated in the Tables, but not necessarily in the relative intensities specified, which can vary depending on a number of factors as discussed later.

Typically, the crystalline material comprises [AlO$_4$] and [PO$_4$] corner sharing tetrahedral units and conveniently also comprises [SiO$_4$] corner sharing tetrahedral units.

Conveniently, in its as-synthesized form and on an anhydrous basis, the porous, crystalline material is represented by the empirical formula:

$$mR:F_a:(M_xAl_yP_z)O_2$$

wherein R represents at least one directing agent, preferably 4-dimethylaminopyridine; m is the number of moles of R per mole of $(M_xAl_yP_z)O_2$ and has a value from about 0 to about 1, such as from about 0 to about 0.5, for example from about 0 to about 0.3; wherein a is the number of moles of fluoride ion (F) per mole of $(M_xAl_yP_z)O_2$ and has a value of about 0 to about 1, such as from about 0.1 to about 0.8, for example from about 0.2 to about 0.6; wherein x, y, and z represent the respective mole fractions of M, Al and P as tetrahedral oxides; and wherein M is a metal selected from one of Groups 1 to 14 and Lanthanoids of the Periodic Table of Elements. Preferably M is selected from B, Co, Cr, Cu, Fe, Ga, Ge, Mg, Mn, Ni, Si, Sn, Ti, Zn and/or Zr and most preferably, M is silicon. In one embodiment, x is from 0 to about 0.25, y is from about 0.3 to about 0.7 and z is from about 0.25 to about 0.7. In another embodiment, x is from about 0 to about 0.15, y is from about 0.4 to about 0.6 and z is from about 0.3 to about 0.6. In yet another embodiment x is from about 0 to about 0.12, y is from about 0.45 to about 0.55 and z is from about 0.35 to about 0.55. For ALPO molecular sieves, x is zero.

In another aspect, the invention resides in a method of synthesizing the crystalline material of said one aspect of the invention, the process comprising: (a) forming a reaction mixture comprising a source of aluminum, a source of phosphorus, a source of fluoride ions, optionally a source of metal M, and at least one structure directing agent comprising 4-dimethylaminopyridine such that said reaction mixture has a F/Al$_2$O$_3$ molar ratio of at least 0.75, such as greater than 0.75 to about 2.5, for example from 0.85 to 2.0 and conveniently from 1.0 to 1.5; (b) inducing crystallization of said crystalline material from the reaction mixture; and (c) recovering said crystalline material from the reaction mixture.

In still a further aspect, the invention resides in the use of the crystalline material of said one aspect of the invention as a sorbent or as a catalyst in organic conversion reactions.

DETAILED DESCRIPTION OF THE EMBODIMENTS

In one embodiment, the present invention relates to a novel porous crystalline (metallo)aluminophosphate material, such as a SAPO and AlPO$_4$, its synthesis in the presence of fluoride ions and the organic directing agent, 4-dimethylaminopyridine, and its use as a catalyst in organic conversion reactions. The crystalline structure remains intact after calcination to remove the directing agent and adsorption data suggest that the calcined material may have small, slit-like pore openings. In particular, the calcined material does not adsorb 2,2-dimethylbutane, but does adsorb methanol, n-hexane, and a small amount of mesitylene. The SAPO version of the material has methanol conversion activity and n-hexane cracking activity.

The porous, crystalline material of the invention comprises at least [AlO$_4$] and [PO$_4$] corner sharing tetrahedral units, and preferably [SiO$_4$], [AlO$_4$] and [PO$_4$] corner sharing tetrahedral units, and has, in its as-synthesized form, an X-ray diffraction pattern including the lines listed in Table 1 below:

TABLE 1

| 2-Theta | d, nm | Relative Intensity |
| --- | --- | --- |
| 6.16 ± 0.05 | 1.43 ± .0.012 | VS |
| 8.92 ± 0.05 | 0.991 ± 0.006 | M |
| 12.84 ± 0.05 | 0.689 ± 0.003 | M |
| 13.98 ± 0.05 | 0.633 ± 0.003 | S |
| 14.32 ± 0.05 | 0.618 ± 0.002 | M |
| 18.04 ± 0.05 | 0.491 ± 0.002 | W |
| 19.26 ± 0.05 | 0.460 ± 0.001 | W |
| 19.88 ± 0.05 | 0.446 ± 0.001 | W |
| 20.44 ± 0.05 | 0.434 ± 0.001 | VS |
| 21.36 ± 0.05 | 0.416 ± 0.001 | W |
| 23.18 ± 0.05 | 0.383 ± 0.001 | W |
| 24.42 ± 0.05 | 0.364 ± 0.001 | M |
| 25.58 ± 0.05 | 0.348 ± 0.001 | S |
| 26.08 ± 0.05 | 0.341 ± 0.001 | M |
| 26.68 ± 0.05 | 0.334 ± 0.001 | M |
| 28.02 ± 0.05 | 0.318 ± 0.001 | W |
| 28.32 ± 0.05 | 0.315 ± 0.001 | W |
| 29.14 ± 0.05 | 0.306 ± 0.001 | W |
| 30.22 ± 0.05 | 0.295 ± 0.001 | W |
| 35.28 ± 0.05 | 0.254 ± 0.001 | W |

In its as-calcined form, the porous, crystalline material of the invention has an X-ray diffraction pattern including the lines listed in Table 2 below:

TABLE 2

| 2-Theta | d, nm | Relative Intensity |
| --- | --- | --- |
| 7.34 ± 0.05 | 1.203 ± 0.008 | VS |
| 12.64 ± 0.05 | 0.700 ± 0.003 | S |
| 14.14 ± 0.05 | 0.626 ± 0.003 | M |
| 19.80 ± 0.05 | 0.448 ± 0.002 | M |
| 22.90 ± 0.05 | 0.388 ± 0.001 | W |
| 26.06 ± 0.05 | 0.342 ± 0.001 | S |
| 28.16 ± 0.05 | 0.317 ± 0.001 | W |
| 35.24 ± 0.05 | 0.254 ± 0.001 | W |
| 35.64 ± 0.05 | 0.252 ± 0.001 | W |

These, and all other X-ray diffraction data referred to herein, were collected with a Siemens D500 diffractometer with a voltage of 40 kV and a current of 30 mA using a copper target (λ=0.154 nm) and a curved graphite monochrometer. The diffraction data were recorded by step-scanning at 0.02 degrees of two-theta, where theta is the Bragg angle, and a counting time of 1 second for each step. The interplanar spacings, d's, were calculated in nanometres (nm), and the relative intensities of the lines, I/Io, where Io is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (75-100), s=strong (50-74), m=medium (25-49) and w=weak (0-24). It should be understood that diffraction data listed for this sample as single lines may consist of multiple overlapping lines which under certain conditions, such as differences in crystallite sizes or very high experimental resolution or crystallographic change, may appear as resolved or partially resolved lines. Typically, crystallographic changes can include minor changes in unit cell parameters and/or a change in crystal symmetry, without a change in topology of the structure. These minor effects, including changes in relative intensities, can also occur as a result of differences in cation content, framework composition, nature and degree of pore filling, and thermal and/or hydrothermal history. In practice, therefore, at least some of the lines in the X-ray patterns of the crystalline material of the invention may exhibit significant variations in relative intensity from the values indicated in Tables 1 and 2.

To generate the as-calcined X-ray data listed in Table 2, about 0.5 grams of the dried, as-synthesized crystalline material are heated in an oven from room temperature under a flow of nitrogen at a rate of 10° C./minute to 400° C. and, while retaining the nitrogen flow, the sample is held at 400° C. for 30 minutes. The nitrogen flow is then ceased and air is passed over the sample while the temperature of the oven is raised at a rate of 10° C./minute to 600° C. The sample is then retained at 600° C. for 2 hours under air, whereafter the oven is cooled to room temperature to allow the XRD pattern to be recorded.

In its as-synthesized form and on an anhydrous basis, the porous, crystalline material of the present invention can be represented by the empirical formula:

$$mR:F_a:(M_xAl_yP_z)O_2$$

wherein R represents at least one directing agent, preferably an organic directing agent and most preferably 4-dimethylaminopyridine, m is the number of moles of R per mole of $(M_xAl_yP_z)O_2$ and m has a value from about 0 to about 1, such as from about 0 to about 0.5, for example from 0 to about 0.3; wherein F represents fluoride ion, a is the number of moles of F per mole of $(M_xAl_yP_z)O_2$ and a has a value of 0 to 1, such as from 0.1 to 0.8, for example from 0.2 to 0.6; wherein x, y, and z represent the mole fraction M, Al and P as tetrahedral oxides; and wherein M is a metal selected from one of Groups 1 to 14 and Lanthanoids of the Periodic Table of Elements. Preferably M is selected from B, Co, Cr, Cu, Fe, Ga, Ge, Mg, Mn, Ni, Si, Sn, Ti, Zn, Zr and mixtures thereof. Most preferably, M is silicon.

In one embodiment, x is from 0 to about 0.25, y is from about 0.3 to about 0.7 and z is from about 0.25 to about 0.7. In another embodiment x is from about 0 to about 0.15, y is from about 0.4 to about 0.6 and z is from about 0.3 to about 0.6. In yet another embodiment x is from about 0 to about 0.12, y is from about 0.45 to about 0.55 and z is from about 0.35 to about 0.55. For ALPO molecular sieves, x is zero.

It will be appreciated that the R and F components, which are associated with the as-synthesized material as a result of their presence during crystallization, are easily removed by post-crystallization methods hereinafter more particularly described.

The silicoaluminophosphate of the present invention typically has an alpha value of at least 0.1, and more preferably at least 0.5, indicating that the material is useful as an acid catalyst in organic conversion reactions. The alpha value test is a measure of the cracking activity of a catalyst and is described in U.S. Pat. No. 3,354,078 and in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

The porous crystalline material of the present invention can be produced from a synthesis mixture containing water, a source of phosphorus, a source of aluminum, a source of fluoride ions, optionally a source of metal M, such as silicon, and 4-dimethylaminopyridine (R). The synthesis mixture typically has a composition, expressed in terms of mole ratios of oxides, as follows:

| Component | Useful | Preferred |
|---|---|---|
| $P_2O_5:Al_2O_3$ | 0.7 to 1.3 | 0.9 to 1.1 |
| $SiO_2:Al_2O_3$ | 0 to 0.9 | 0.05 to 0.5 |
| $H_2O:Al_2O_3$ | 10 to 100 | 20 to 60 |
| $R:Al_2O_3$ | 0.5 to 5.0 | 1.0 to 4.0 |
| $F:Al_2O_3$ | $\geq 0.75$ to 3 | >0.75 to 2.5 |

More specifically, $F/Al_2O_3$ molar ratio of the synthesis mixture is from 0.85 to 2.0, such as from 1.0 to 1.5

A suitable source of phosphorus in the above mixture is phosphoric acid. Examples of suitable aluminum sources include hydrated aluminum oxides such as boehmite, pseudoboehmite, and aluminum trialkoxide. Suitable sources of silicon include silicates, e.g., fumed silica, such as Aerosil and Cabosil, tetraalkyl orthosilicates, and aqueous colloidal suspensions of silica, for example that sold by E.I. du Pont de Nemours under the tradename Ludox.

The source of fluoride ions may be any compound capable of releasing fluoride ions in the synthesis mixture. Non-limiting examples of such sources of fluoride ions include salts containing one or several fluoride ions, such as metal fluorides, preferably, sodium fluoride, potassium fluoride, calcium fluoride, magnesium fluoride, strontium fluoride, barium fluoride, ammonium fluoride, tetraalkylammonium fluorides, such as tetramethylammonium fluoride, tetraethylammonium fluoride, hydrogen fluoride, fluorosilicic acid, hexafluorophosphoric acid, and mixtures thereof. Most preferably, the source of fluoride is hydrogen fluoride.

Crystallization is carried out under either stirred or static conditions, preferably stirred conditions, at a temperature between about 100° C. and about 250° C., typically between about 130° C. and about 200° C., preferably between about 150° C. and about 180° C. Preferably, crystallization is conducted for about 2 to about 150 hours, preferably about 20 to about 100 hours, whereafter the resultant crystalline material is separated from the mother liquor and recovered, such as by centrifugation or filtration. The separated product can also be washed, recovered by centrifugation or filtration and dried. The crystalline product is typically in the form of platelets having a $d_{50}$ (50% by volume of crystals is smaller than the $d_{50}$ value) particle size less than 1 μm.

Synthesis of the small pore (metallo)aluminophosphate material of the invention may be facilitated by the presence of at least 0.1 ppm, such as at least 10 ppm, for example at least 100 ppm, conveniently at least 500 ppm of seed crystals from a previous synthesis based on total weight of the reaction mixture.

As a result of the crystallization process, the recovered crystalline product contains within its pores at least a portion of the organic directing agent used in the synthesis. In a preferred embodiment, activation is performed in such a manner that the organic directing agent is removed from the molecular sieve, leaving active catalytic sites within the microporous channels of the molecular sieve open for contact with a feedstock. The activation process is typically accomplished by calcining, or essentially heating the molecular sieve comprising the template at a temperature of from about 200° C. to about 800° C., typically in the presence of an oxygen-containing gas. This type of process can be used for partial or complete removal of the organic directing agent from the intracrystalline pore system.

Once the crystalline material of the invention has been synthesized, it can be formulated into a catalyst composition by combination with other materials, such as binders and/or matrix materials, that provide additional hardness or catalytic activity to the finished catalyst.

Materials which can be blended with the crystalline material of the invention can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of intergrown crystalline material contained in the final catalyst product ranges from 10 to 90 weight percent of the total catalyst, preferably 20 to 80 weight percent of the total catalyst.

The small pore crystalline material described herein can be used to dry gases and liquids; for selective molecular separation based on size and polar properties; as an ion-exchanger; as a catalyst in organic conversion reactions, such as cracking, hydrocracking, disproportionation, alkylation, isomerization, oxidation and synthesis of monoalkylamines and dialkylamines; as a chemical carrier; in gas chromatography; and in the petroleum industry to remove normal paraffins from distillates.

In particular, the small pore crystalline material described herein is useful in the catalytic conversion of oxygenates to one or more olefins, particularly ethylene and propylene. As used herein, the term "oxygenates" is defined to include, but is not necessarily limited to aliphatic alcohols, ethers, carbonyl compounds (aldehydes, ketones, carboxylic acids, carbonates, and the like), and also compounds containing heteroatoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally with one or more diluents, is contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 hr$^{-1}$ to about 500 hr$^{-1}$, such as in the range of from about 0.5 hr$^{-1}$ to about 300 hr$^{-1}$, for example in the range of from about 0.1 hr$^{-1}$ to about 200 hr$^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

In order to more fully illustrate the nature of the invention and the manner of practicing same, the following Examples are presented. In the Examples, elemental analysis of Al, Si, and P was performed using Inductively Coupled Plasma (ICP) spectroscopy.

EXAMPLE 1

The following ingredients were mixed, in sequence, and blended into a uniform gel using a microhomogenizer (Tissue Tearor Model 98730, available from Biospec Products, Inc, USA): 85 wt % $H_3PO_4$ (obtained from Aldrich Chemical Company), deionized $H_2O$, Catapal™ A (73.9 wt % $Al_2O_3$, available from CONDEA Vista Company, Texas, USA), 50 wt % HF in water (Aldrich Chemical Company), and then 4-dimethylaminopyridine (4-DMAPy) (obtained from Aldrich Chemical Company, USA). The molar ratio of the ingredients was as follows:

$1.0HF:2.0DMAPy:1.0Al_2O_3:1.0P_2O_5:40H_2O$

Figure 1:
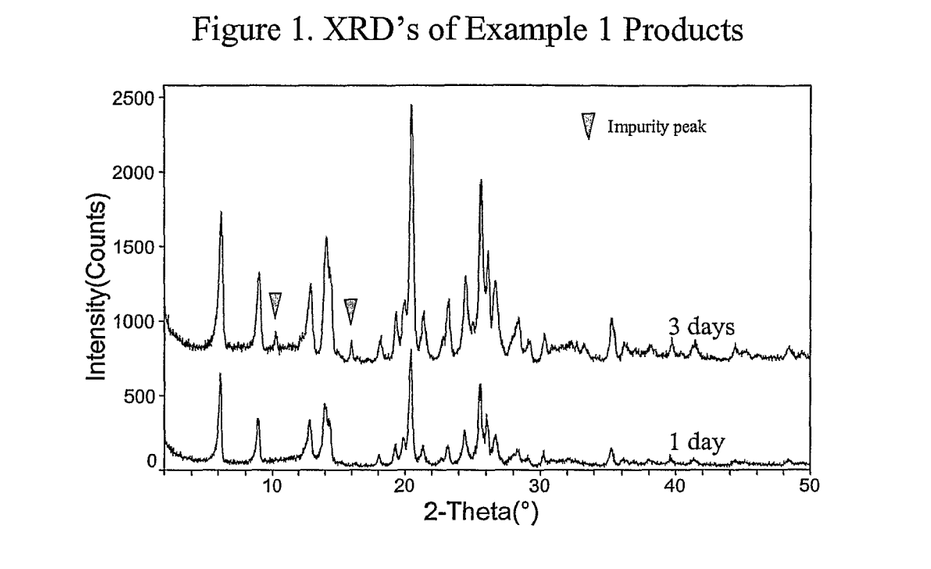
FIG. 1 gives the X-ray diffraction patterns of the as-synthesized products of Example 1 after crystallization for 1 day and 3 days.

The gel was then placed into a Parr bomb with Teflon liner, and was heated to 180° C. for 1 to 3 days statically. The solid product was centrifuged and washed five times with deionized water, and was then dried in a 60° C. vacuum oven overnight. X-ray powder patterns of the product showed, in FIG. 1, that a crystalline product was obtained after one day of crystallization (Sample A). After three days of crystallization, additional diffraction peaks corresponding to an unidentified impurity appeared.

Solid product yield of Sample A was 13.6%, based on the total weight of the starting gel. Elemental analysis gave the following results: Al, 13.31%; P, 14.94%. These results corresponded to $Al_{1.0}P_{0.978}$ in composition and 59.4% for calculated total oxides.

The XRD pattern of Sample A had no match with any known patterns. The peak list is shown in Table 3 below.

TABLE 3

| 2-Theta | D, nm | I % |
|---|---|---|
| 6.16 | 1.433 | 83 |
| 8.92 | 0.991 | 42 |
| 12.84 | 0.689 | 35 |
| 13.98 | 0.633 | 53 |
| 14.32 | 0.618 | 39 |
| 18.04 | 0.491 | 10 |
| 19.26 | 0.460 | 18 |
| 19.88 | 0.446 | 23 |

TABLE 3-continued

| 2-Theta | D, nm | I % |
|---|---|---|
| 20.44 | 0.434 | 100 |
| 21.36 | 0.416 | 17 |
| 23.18 | 0.383 | 16 |
| 24.42 | 0.364 | 32 |
| 25.58 | 0.348 | 66 |
| 26.08 | 0.341 | 37 |
| 26.68 | 0.334 | 26 |
| 28.02 | 0.318 | 7 |
| 28.32 | 0.315 | 12 |
| 29.14 | 0.306 | 7 |
| 30.22 | 0.295 | 11 |
| 32.10 | 0.279 | 3 |
| 35.28 | 0.254 | 15 |
| 36.08 | 0.249 | 5 |
| 37.98 | 0.237 | 5 |
| 39.60 | 0.227 | 6 |
| 41.36 | 0.218 | 5 |
| 44.42 | 0.204 | 5 |

EXAMPLE 2

The procedure of Example 1 was repeated, except that varying amounts of hydrofluoric acid were added to produce four different synthesis mixtures having the following molar ratio of ingredients:

$xHF:2.0DMAPy:1.0Al_2O_3:1.0P_2O_5:40H_2O$ where x=0.5, 0.625, 0.75 and 0.875.

Figure 2:
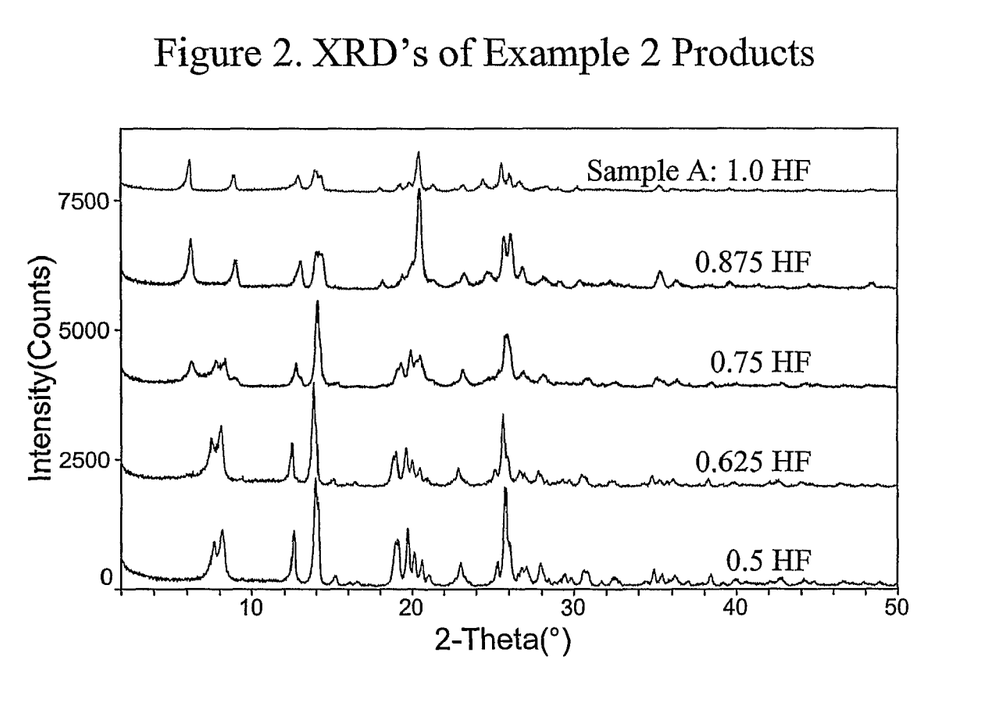
FIG. 2 gives the X-ray diffraction patterns of the as-synthesized products of Example 2 with varying F/Al$_2$O$_3$ molar ratios.

In each case, the crystallization was carried out for one to two days at 180° C. statically. The XRD patterns of the products are shown in FIG. 2 along with that of Sample A. FIG. 2 shows that, at an $HF/Al_2O_3$ molar ratio less than 0.75, the new framework material disclosed in co-pending U.S. Patent Application Ser. No. 60/615,111 was formed. At $HF/Al_2O_3$ molar ratios greater than 0.75, the new phase of this invention was formed. When the $HF/Al_2O_3$ molar ratio was equal to 0.75, a mixture of the two phases was produced.

Elemental analysis of the product obtained with $HF/Al_2O_3$ molar ratio of 0.875 gave the following results: Al, 12.2%; P, 14.2%. These results corresponded to $Al_{1.0}P_{1.014}$ in composition and 56.4% for calculated total oxides.

EXAMPLE 3

The procedure was identical to Example 2, except that a higher amount of hydrofluoric acid was added and the ingredient ratio was the following:

$2.0HF:2.0DMAPy:1.0Al_2O_3:1.0P_2O_5:40H_2O$

Figure 3:
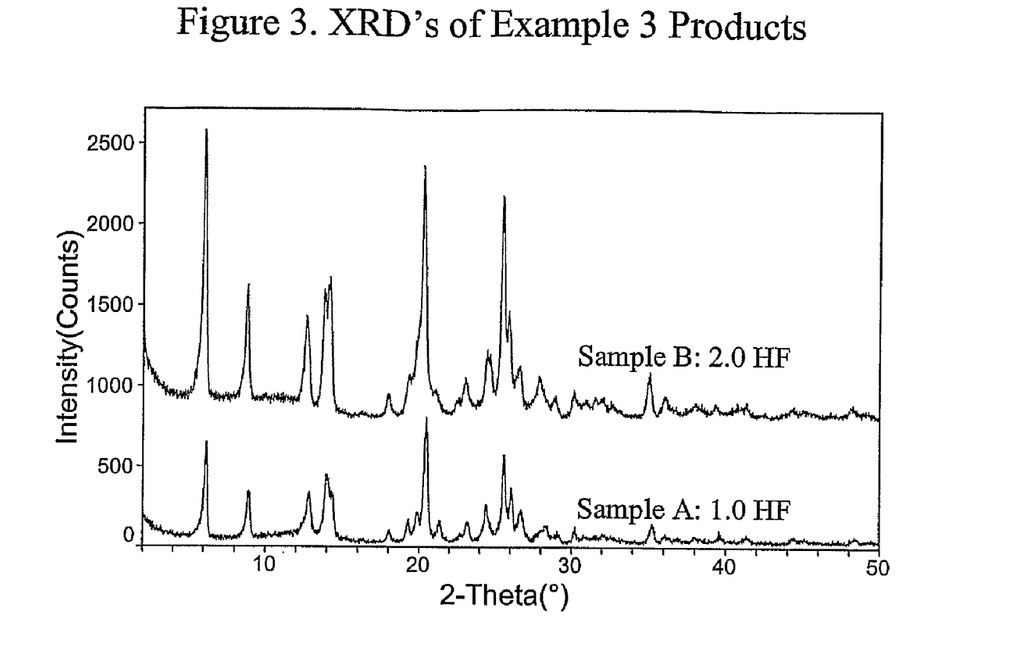
FIG. 3 is a comparison of the X-ray diffraction patterns of Sample A in Example 1 and Sample B in Example 3.

Crystallization was carried out for two days at 170° C. with tumbling at 40 rpm. The product yield was 10.0% based on the total weight of the gel. The XRD pattern of the product (Sample B) is shown in FIG. 3, along with that of Sample A. FIG. 3 shows that Sample B is the same crystalline phase as Sample A. Elemental analysis of Sample B gave the following results: Al, 13.3%; P, 15.1%. These results corresponded to $Al_{1.0}P_{0.989}$ in composition and 59.8% for calculated total oxides.

This example, along with Example 2, shows that products of this invention, having the same XRD pattern, can be obtained with variations in both gel composition and in reaction conditions. These results establish that the product of this invention is a phase-pure material.

EXAMPLE 4

The procedure was identical to Example 1, except that silica in the form of Cabosil™ (Cabot Corporation, Illinois, USA) was added after the addition of Catapal and before the addition of HF. The ingredient ratio was the following:

$$1.0HF:2.0DMAPy:1.0Al_2O_3:0.5SiO_2:1.0P_2O_5:40H_2O$$

0.1 wt % (with respect to the weight of the gel) of Sample A was added to the synthesis gel as seeds and crystallization was carried out for one day and two days, respectively, at 170° C. with tumbling at 40 rpm. The XRD patterns of the products are shown in FIG. 4, along with that of sample B.

Figure 4:
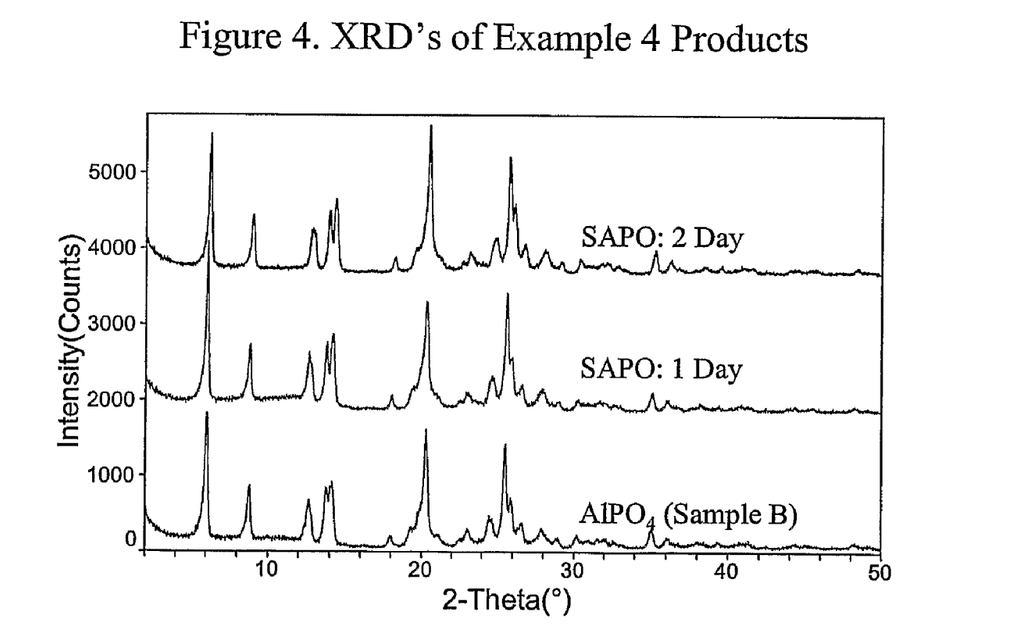
FIG. 4 is a comparison of the X-ray diffraction pattern of Sample B in Example 3 (ALPO) with the X-ray diffraction pattern of the as-synthesized SAPO products of Example 4 after crystallization for 1 day (Sample C) and 2 days.

FIG. 4 shows that the SAPO products have the same framework structure as Sample B (an $AlPO_4$). Elemental analysis of the SAPO sample obtained after one day of crystallization (Sample C) gave the following results: Al, 12.6%; Si, 3.67%; P, 12.7%. These results corresponded to $Al_{1.0}Si_{0.280}P_{0.878}$ in composition and 62.2% for calculated total oxides. TGA (Thermal Gravimetric Analysis) revealed a non-combustible residual weight of 62.79%.

EXAMPLE 5

To effect removal of the organic directing agent, Samples A, B, and C were placed in a muffle furnace and the temperature was ramped at 10° C./minute to 400° C. while the furnace was flushed with nitrogen. After dwelling at 400° C. for 30 minutes, the temperature ramping was continued, and the flowing gas was switched from nitrogen to air. The temperature ramp stopped at 650° C. and the sample was calcined at this temperature for two hours under flowing air. During the entire calcination process the sample turned dark brown first, finally to slightly off-white. The XRD patterns of the calcined samples are shown in FIG. 5.

Figure 5:
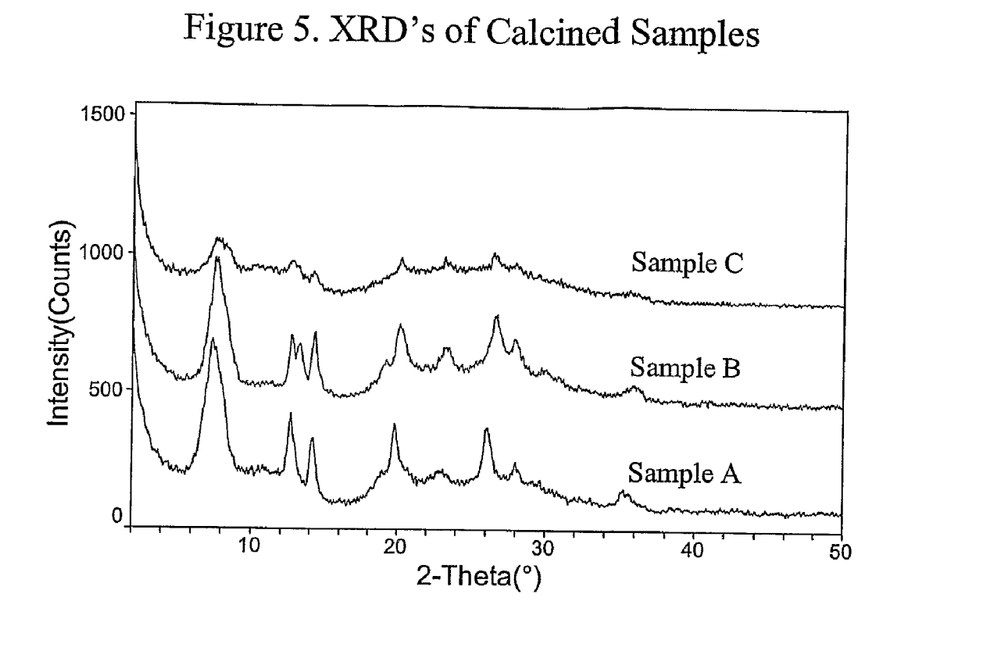
FIG. 5 is a comparison of the X-ray diffraction patterns of Samples A, B and C after calcination at 650° C. for 2 hours as described in Example 5.

FIG. 5 shows that the calcined samples have only broad peaks. The peaks include at least the following (Table 4):

TABLE 4

| 2-Theta | d, nm | I % |
| --- | --- | --- |
| 7.34 | 1.203 | 100 |
| 12.64 | 0.700 | 63 |
| 14.14 | 0.626 | 50 |
| 19.80 | 0.448 | 50 |
| 22.90 | 0.388 | 11 |
| 26.06 | 0.342 | 51 |
| 28.16 | 0.317 | 11 |
| 35.24 | 0.254 | 14 |
| 35.64 | 0.252 | 11 |

Figure 6:
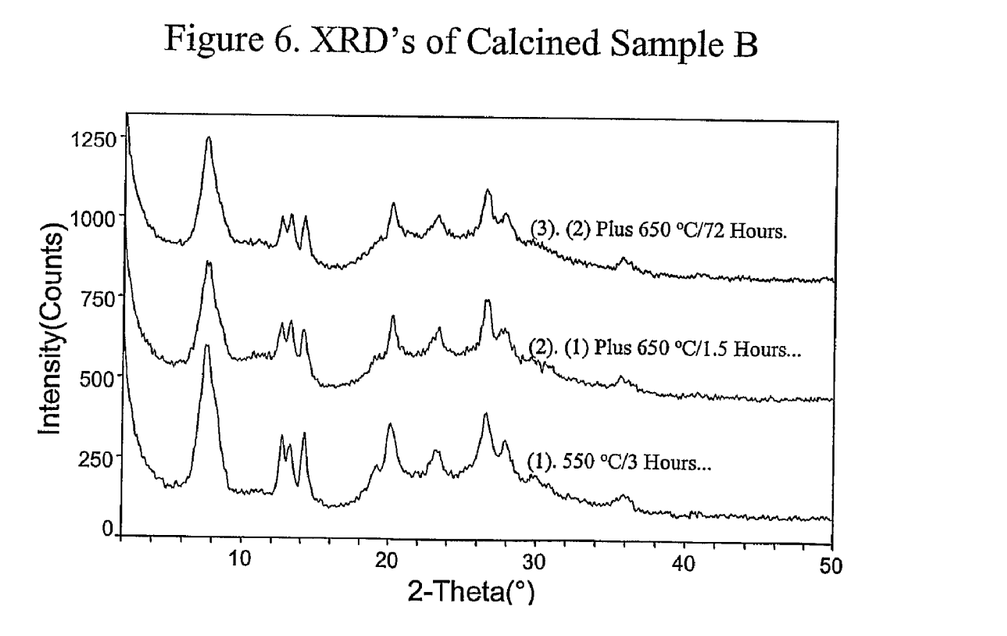
FIG. 6 is a comparison of the X-ray diffraction patterns of Sample B after calcination at varying temperatures and times as described in Example 5.

To test the thermal stability of the material, Sample B was calcined under conditions of different thermal severity. FIG. 6 shows the XRD patterns of the sample B following calcination at 550° C. for three hours, then after calcination at 650° C. for an additional one and half hours, and then after calcination at 650° C. for 72 more hours. FIG. 6 shows that there is hardly any change with these thermal treatments, indicating the material is at least stable to 650° C.

EXAMPLE 6

Sample A was calcined at 500° C. or 600° C. for two hours and then degassed (at 500° C.) before being exposed to different adsorbate molecules under specified conditions as listed in Table 5 below in a Thermal Gravimetric Analysis (TGA) unit. The weight gain (or the lack of) of the sample was recorded, from which adsorption capacity was calculated and expressed as percent of "gram adsorbed per gram of calcined sample". Table 5 summarizes the results of the adsorption experiments.

TABLE 5

| | Sample A | | | | |
| --- | --- | --- | --- | --- | --- |
| Calcination, ° C. | 600 | 500 | 600 | 600 | 600 |
| Adsorbate | Methanol | n-Hexane | n-Hexane | 2,2-DMB | Mesitylene |
| Ads. Conditions | 35° C., 203 torr | 90° C., 75 torr | 90° C., 75 torr | 120° C., 90 torr | 100° C., 2 torr |
| Ads. Capacity, wt % | 14.24 | 6.02 | 2.03 | 0 | 1.02 |

The data in Table 5 show that the new material is porous, having pore openings large enough to allow molecules with kinetic diameter less than 0.43 nm (4.3 Å), such as n-hexane and methanol, to be adsorbed. The pore size is apparently very close to the kinetic diameter of n-hexane, as the calcination temperature affects the amount adsorbed. Without wishing to be bound by theory, it is conjectured that the pore opening is likely to be slit-like, rather than circular, because a small but significant amount of mesitylene (a flat molecule) is adsorbed whereas 2,2-dimethylbutane (2,2-DMB) is not. These adsorption characteristics and the gross change of XRD pattern caused by calcination suggest a condensed layer structure for the calcined phase.

EXAMPLE 7

Sample C was calcined as described in Example 5, but was held at 600° C. for 2 hours in air. The powder was pelletized to 14-25 mesh size for the alpha test (a standard n-hexane cracking test conducted at 1000° F. (540° C.) and fixed n-hexane partial pressure). Such test gave an alpha value of 5.2 for the material. For comparison, a diffusionally unconstrained material, such as SAPO-11, at similar Si/Al ratio as Sample C, typically has an alpha value of greater than 20. The low alpha value of the new material suggests steric hindrance for n-hexane to access the interior of the material, just as the adsorption data also suggest.

EXAMPLE 8

Sample C, after calcination in air at 650° C. for 2 hours, was tested for methanol-to-olefins (MTO) conversion. Methanol liquid was fed via a pump and was vaporized before contacting the catalyst, which was held at 475° C. The methanol pressure was 276 kPa (40 psia) and its feed rate was 100 WHSV. The product effluent was sampled with a multi-port sampling loop during a non-steady-state run (catalyst is continuously deactivated during the MTO run) and each port was analyzed with a Gas Chromatograph equipped with an FID detector. The coke selectivity was calculated with an algorithm reiterated to attain the same H/C ratio in the products as in the feed. Table 6 lists the key MTO reactivity data, along with the product selectivity averaged over the entire run.

TABLE 6

| g MeOH converted/g Sieve | Init. Conv. % | Average Product Selectivity, wt % | | | | | | | | | | |
|---|---|---|---|---|---|---|---|---|---|---|---|---|
| | | $CH_4$ | $C_2=$ | $C_2-$ | $C_3=$ | $C_3-$ | $1-C_4$ | $1-C_4=$ | $2-C_4=$ | $C_5$ | $C_6+$ | Coke |
| 1.68 | 69.5 | 2.37 | 18.69 | 0.47 | 33.94 | 4.61 | 0.48 | 5.35 | 13.69 | 4.89 | 1.03 | 13.73 |

Data in Table 6, along with the alpha test results, indicate that the new material is active for catalytic transformations of organic compounds.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A crystalline aluminophosphate molecular sieve material, having in its calcined form, an X-ray diffraction pattern including the lines listed in Table 2 below:

TABLE 2

| 2-Theta | d, nm | Relative Intensity |
|---|---|---|
| 7.34 ± 0.05 | 1.203 ± 0.008 | VS |
| 12.64 ± 0.05 | 0.700 ± 0.003 | S |
| 14.14 ± 0.05 | 0.626 ± 0.003 | M |
| 19.80 ± 0.05 | 0.448 ± 0.002 | M |
| 22.90 ± 0.05 | 0.388 ± 0.001 | W |
| 26.06 ± 0.05 | 0.342 ± 0.001 | S |
| 28.16 ± 0.05 | 0.317 ± 0.001 | W |
| 35.24 ± 0.05 | 0.254 ± 0.001 | W |
| 35.64 ± 0.05 | 0.252 ± 0.001 | W. |

2. The crystalline material of claim 1 further comprising [$AlO_4$] and [$PO_4$] corner sharing tetrahedral units.

3. The crystalline material of claim 2 further comprising [$SiO_4$] corner sharing tetrahedral units.

4. A crystalline aluminophosphate molecular sieve material, in its as-synthesised form, an X-ray diffraction pattern including the lines listed in Table 1 below:

TABLE 1

| 2-Theta | d, nm | Relative Intensity |
|---|---|---|
| 6.16 ± 0.05 | 1.43 ± 0.012 | VS |
| 8.92 ± 0.05 | 0.991 ± 0.006 | M |
| 12.84 ± 0.05 | 0.689 ± 0.003 | M |
| 13.98 ± 0.05 | 0.633 ± 0.003 | S |
| 14.32 ± 0.05 | 0.618 ± 0.002 | M |
| 18.04 ± 0.05 | 0.491 ± 0.002 | W |
| 19.26 ± 0.05 | 0.460 ± 0.001 | W |
| 19.88 ± 0.05 | 0.446 ± 0.001 | W |
| 20.44 ± 0.05 | 0.434 ± 0.001 | VS |
| 21.36 ± 0.05 | 0.416 ± 0.001 | W |
| 23.18 ± 0.05 | 0.383 ± 0.001 | W |
| 24.42 ± 0.05 | 0.364 ± 0.001 | M |
| 25.58 ± 0.05 | 0.348 ± 0.001 | S |
| 26.08 ± 0.05 | 0.341 ± 0.001 | M |
| 26.68 ± 0.05 | 0.334 ± 0.001 | M |
| 28.02 ± 0.05 | 0.318 ± 0.001 | W |
| 28.32 ± 0.05 | 0.315 ± 0.001 | W |
| 29.14 ± 0.05 | 0.306 ± 0.001 | W |
| 30.22 ± 0.05 | 0.295 ± 0.001 | W |
| 35.28 ± 0.05 | 0.254 ± 0.001 | W. |

5. The crystalline material of claim 4 is represented by the empirical formula, on an anhydrous basis:

$$mR:F_a:(M_xAl_yP_z)O_2$$

wherein R represents at least one directing agent; wherein m is the number of moles of R per mole of $(M_xAl_yP_z)O_2$; wherein a is the number of moles of fluoride ion (F) per mole of $(M_xAl_yP_z)O_2$; wherein x, y, and z represent the mole fraction of M, Al and P as tetrahedral oxides; and wherein M is a metal selected from one of Groups 1 to 14 and Lanthanoids of the Periodic Table of Elements.

6. The crystalline material of claim 5 wherein m has a value from about 0 to about 1.

7. The crystalline material of claim 6 wherein R is 4-dimethylaminopyridine.

8. The crystalline material of claim 5 wherein R is 4-dimethylaminopyridine.

9. The crystalline material of claim 8 wherein a has a value from about 0 to about 1.

10. The crystalline material of claim 9 wherein M is selected from one of the group consisting of B, Co, Cr, Cu, Fe, Ga, Ge, Mg, Mn, Ni, Si, Sn, Ti, Zn, Zr and mixtures thereof.

11. The crystalline material of claim 9 wherein x is from 0 to about 0.25, y is from about 0.3 to about 0.7, and z is from about 0.25 to about 0.7.

12. The crystalline material of claim 8 wherein M is selected from one of the group consisting of B, Co, Cr, Cu, Fe, Ga, Ge, Mg, Mn, Ni, Si, Sn, Ti, Zn, Zr and mixtures thereof.

13. The crystalline material of claim 8 wherein x is from 0 to about 0.25, y is from about 0.3 to about 0.7, and z is from about 0.25 to about 0.7.

14. The crystalline material of claim 5 wherein a has a value from about 0 to about 1.

15. The crystalline material of claim 5 wherein a has a value from 0.2 to 0.6.

16. The crystalline material of claim 5 wherein M is selected from one of the group consisting of B, Co, Cr, Cu, Fe, Ga, Ge, Mg, Mn, Ni, Si, Sn, Ti, Zn, Zr and mixtures thereof.

17. The crystalline material of claim 5 wherein M is silicon.

18. The crystalline material of claim 5 wherein x is from 0 to about 0.25, y is from about 0.3 to about 0.7, and z is from about 0.25 to about 0.7.

19. A method of synthesizing the crystalline material of claim 1 or 4, the process comprising: (a) forming a reaction mixture comprising a source of aluminum, a source of phosphorus, a source of fluoride ions, optionally a source of metal M, and at least one structure directing agent comprising 4-dimethylaminopyridine such that said reaction mixture has a $F/Al_2O_3$ mole ratio of at least 0.75; (b) inducing crystallization of said crystalline material from the reaction mixture; and (c) recovering said crystalline material from the reaction mixture.

20. The method of claim 19 wherein the reaction mixture has a composition, in terms of mole ratios, within the following ranges:

$P_2O_5:Al_2O_3$=0.7 to 1.3
$Si_2O_5:Al_2O_3$=0 to 0.9

$H_2O:Al_2O_3 = 10$ to $100$
$R:Al_2O_3 = 0.5$ to $5.0$
$F:Al_2O_3 = \geqq 0.75$ to $3$.

21. The method of claim 20 wherein the reaction mixture has a composition, in terms of mole ratios, within the following ranges:

$P_2O_5:Al_2O_3 = 0.9$ to $1.1$
$Si_2O_5:Al_2O_3 = 0.05$ to $0.5$
$H_2O:Al_2O_3 = 20$ to $60$
$R:Al_2O_3 = 1.0$ to $4.0$
$F:Al_2O_3 = >0.75$ to $2.5$.

22. The method of claim 19, wherein the reaction mixture has an $F/Al_2O_3$ mole ratio of about 0.85 to about 2.0.

23. The method of claim 19, wherein crystallization of said crystalline material is conducted at a temperature of about 100° C. to about 250° C.

24. The method of claim 23, wherein crystallization of said crystalline material is conducted at a temperature of 130° C. to 200° C.

25. An organic conversion process comprising contacting an organic feedstock with a catalyst comprising the crystalline material according to claim 1 or 4.

26. The process of claim 25 wherein an oxygenate-containing feedstock is converted to olefins.

27. An organic conversion process comprising contacting an organic feedstock with a catalyst comprising the crystalline material produced by the method of claim 19.

28. The process of claim 27 wherein an oxygenate-containing feedstock is converted to olefins.

* * * * *